US012285207B2

(12) United States Patent
van der Weide et al.

(10) Patent No.: US 12,285,207 B2
(45) Date of Patent: *Apr. 29, 2025

(54) ENERGY DELIVERY SYSTEMS AND USES THEREOF

(71) Applicant: NEUWAVE MEDICAL, INC., Madison, WI (US)

(72) Inventors: Daniel Warren van der Weide, Madison, WI (US); Fred T. Lee, Jr., Madison, WI (US); Paul F. Laeseke, Madison, WI (US); Christopher Lee Brace, Madison, WI (US)

(73) Assignee: NEUWAVE MEDICAL, INC., Madison, WI (US)

( * ) Notice: Subject to any disclaimer, the term of this patent is extended or adjusted under 35 U.S.C. 154(b) by 488 days.

This patent is subject to a terminal disclaimer.

(21) Appl. No.: 17/864,049

(22) Filed: Jul. 13, 2022

(65) Prior Publication Data

US 2022/0346873 A1 Nov. 3, 2022

Related U.S. Application Data

(63) Continuation of application No. 11/879,072, filed on Jul. 16, 2007, now Pat. No. 11,389,235.

(60) Provisional application No. 60/831,055, filed on Jul. 14, 2006.

(51) Int. Cl.
*A61B 18/18* (2006.01)
*A61B 18/00* (2006.01)
*A61B 18/14* (2006.01)

(52) U.S. Cl.
CPC .......... *A61B 18/18* (2013.01); *A61B 18/1815* (2013.01); *A61B 2018/00577* (2013.01); *A61B 18/14* (2013.01); *A61B 2018/1425* (2013.01); *A61B 18/1477* (2013.01); *A61B 2018/183* (2013.01); *A61B 2018/1861* (2013.01); *A61B 2018/1869* (2013.01)

(58) Field of Classification Search
CPC ........ A61B 18/1815; A61B 2018/1838; A61B 2018/1846; A61B 2018/1853; A61B 2018/1869
See application file for complete search history.

(56) References Cited

U.S. PATENT DOCUMENTS 5,026,959 A * 6/1991 Ito .......................... A61B 18/18
607/101

FOREIGN PATENT DOCUMENTS

WO WO-2004084748 A1 * 10/2004 ............. A61B 18/18

* cited by examiner

*Primary Examiner* — Jaymi E Della
(74) *Attorney, Agent, or Firm* — Vorys, Sater, Seymour and Pease LLP (57) ABSTRACT

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy with a linear array of antenna components having optimized energy delivery characteristics. In certain embodiments, methods are provided for treating a tissue region (e.g., a tumor) through application of energy with the systems and devices of the present invention.

12 Claims, 2 Drawing Sheets

FIG. 2

ENERGY DELIVERY SYSTEMS AND USES THEREOF

The present application is a continuation of U.S. patent application Ser. No. 11/879,072, filed Jul. 16, 2007, allowed as U.S. Pat. No. 11,389,235, which claims priority to U.S. Provisional Application Ser. No. 60/831,055, filed Jul. 14, 2006, herein incorporated by reference in their entireties.

FIELD OF THE INVENTION

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy with a linear array of antenna components having optimized energy delivery characteristics. In certain embodiments, methods are provided for treating a tissue region (e.g., a tumor) through application of energy with the systems and devices of the present invention.

BACKGROUND

Ablation is an important therapeutic strategy for treating certain tissues such as benign and malignant tumors, cardiac arrhythmias, cardiac dysrhythmias and tachycardia. Most approved ablation systems utilize radio-frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices configured to deliver microwave energy have drawbacks. For example, current devices produce relatively small lesions because of practical limits in power and treatment time. Current devices have power limitations in that the power carrying capacity of the feedlines are small. Larger diameter feedlines are undesirable, however, because they are less easily inserted percutaneously and may increase procedural complication rates. Microwave devices are also limited to single antennas for most purposes thus limiting the ability to simultaneously treat multiple areas or to place several antennas in close proximity to create large zones of tissue heating. In addition, heating of the feedline at high powers can lead to burns around the area of insertion for the device.

Improved systems and devices for delivering energy to a tissue region are needed. In addition, improved systems and devices capable of delivering microwave energy without corresponding microwave energy loss are needed. In addition, systems and devices capable of percutaneous delivery of microwave energy to a subject's tissue without undesired tissue burning are needed. Furthermore, systems for delivery of desired amounts of microwave energy in a multiple-antenna format without requiring physically large invasive components are needed.

SUMMARY OF THE INVENTION

The present invention relates to systems and devices for delivering energy (e.g., microwave energy, radiofrequency energy, ultrasound energy) to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention relates to systems and devices for the delivery of microwave energy through a linear array of antenna components with optimized energy delivery characteristics. In certain embodiments, methods are provided for treating a tissue region (e.g., a tumor) through application of microwave energy with the systems and devices of the present invention. The systems and methods of the present invention provide for control of energy delivery (e.g., delivery of different amounts of energy along the length of a catheter) to precisely sculpt an ablation zone.

The present invention provides systems, devices, and methods that employ components for the delivery of energy (e.g., microwave energy, radiofrequency energy, ultrasound energy) at an optimized characteristic impedance through a linear array of antenna components configured to emit energy from varied locations. In some embodiments, an antenna is provided comprising an inner conductor and an outer conductor, wherein the outer conductor is provided in two or more linear segments separated by gaps, such that the length and position of the segments is configured for optimized delivery of energy at the distal end of the antenna. For example, in some embodiments, an antenna comprises a first segment of outer conductor that spans the proximal end of the antenna to a region near the distal end and a second segment of outer conductor distal to the first segment wherein a gap separates or partially separates the first and second segments. The gaps may entirely circumscribe the outer conductor or may only partially circumscribe the outer conductor. In some embodiments, the length of the second segment is $\lambda/2$, $\lambda/4$, etc., although the present invention is not so limited. In some embodiments one or more additional (e.g., third, fourth, fifth) segments are provided distal to the second segment, each of which is separated from the other by a gap. In some embodiments, the antenna is flexible for purposes of positioning the device around, for example, pulmonary veins and/or tubular structures. In some embodiments, the antenna is terminated with a conductive terminal end that is in electronic communication with the inner conductor. In some embodiments, the conductive terminal end comprises a disc having a diameter substantially identical to the diameter of the outer conductor. Such antenna of the present invention provide multiple peaks of energy delivery along the length of the distal end of the antenna, providing a broader region of energy delivery to target larger regions of tissue. The location and position of the peaks is controlled by selecting the length of the outer conductor segments and by controlling the amount of energy delivered.

In some embodiments, one side of the outer conductor is flat of substantially flat, with the directional pattern radiated from the flat portion to allow the device to seat against the surface of a body.

The present invention is not limited by the nature of the various components of the antenna. A wide variety of components may be used to provide optimal performance, including, but not limited to, the use of a variety of materials for the inner and outer conductors, the use of a variety of materials and configurations for dielectric material between the inner and outer conductors, the use of coolants provided by a variety of different methods.

The present invention is not limited by the type of device or the uses employed. Indeed, the devices may be configured in any desired manner. Likewise, the systems and devices may be used in any application where energy is to be delivered. Such uses include any and all medical, veterinary, and research applications. However, the systems and devices of the present invention may be used in agricultural settings, manufacturing settings, mechanical settings, or any other application where energy is to be delivered.

In some embodiments, the device is configured for percutaneous, intravascular, intracardiac, laparoscopic, or surgical delivery of energy. In some embodiments, the device is configured for delivery of energy to a target tissue or region. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation of any organ (e.g., to treat esophageal pathologies such as Barrett's Esophagus and esophageal adenocarcinoma, endobronchial treatment of lung tumors, intraluminal treatment of colon or small intestinal pathologies), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the device is configured for guided delivery, for example, by computerized tomography, ultrasound, magnetic resonance imaging, fluoroscopy, endoscopy, direct vision, and the like.

In certain embodiments, the device comprises a linear antenna, wherein the linear antenna comprises an outer conductor enveloped around an inner conductor, wherein the inner conductor is designed to receive and transmit energy (e.g., microwave energy, radiofrequency energy, ultrasound energy), wherein the outer conductor has therein a series of gap regions (e.g., at least two) positioned along the outer conductor, wherein the inner conductor is exposed at the gap regions, wherein the energy transmitting along the inner conductor is emitted through the gap regions. The device is not limited to a particular number of gap regions (e.g., 2, 3, 4, 5, 6, 10, 20, 50). In some embodiments, the inner conductor comprises a dielectric layer enveloping a central transmission line. In some embodiments, the dielectric element has near-zero conductivity. In some embodiments, the device further comprises a stylet. In some embodiments, the device further comprises a tuning element for adjusting the amount of energy delivered through the gap regions. In certain embodiments, when used in tissue ablation settings, the device is configured to deliver a sufficient amount of energy to ablate a tissue region or cause thrombosis.

In some embodiments, the size of the device is consistent with a 20-gauge needle or a component of similar diameter to a 20-gauge needle. Preferably, the diameter of the device is not larger than a 16-gauge needle (e.g., no larger than an 18-gauge needle). However, in some embodiments, larger devices are used, as desired. For example, in some embodiments, a device consistent with a 12-gauge needle is provided, or the device can be larger in diameter if mounted on an endoscope, for use during laparoscopic or open surgery, or used under direct vision for superficial structures.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249; each herein incorporated by reference in their entireties.

Thus, in some embodiments, the systems, devices, and methods of the present invention provides an ablation device coupled with a component that provides occlusion of a passageway (e.g., bronchial occlusion). The occlusion component (e.g., inflatable balloon) may be directly mounted on the ablation system or may be used in combination with another component (e.g., an endotracheal or endobronchial tube) associated with the system.

In some embodiments, the devices of the present invention may be mounted onto additional medical procedure devices. For example, the devices may be mounted onto endoscopes, intravascular catheters, or laparoscopes. In some embodiments, the devices are mounted onto steerable catheters.

In some embodiments, one or more components of the systems of the present invention may contain a coating (e.g., Teflon or any other insulator) to help reduce heating or to impart other desired properties to the component or system.

In some embodiments, the device further comprises a tuning element for adjusting the amount of energy delivered to the tissue region. In some embodiments, the tuning element is manually adjusted by a user of the system. In some embodiments, the device is pretuned to the desired tissue and is fixed throughout the procedure. In some embodiments, the tuning element is automatically adjusted and controlled by a processor of the present invention. In some embodiments, the processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

In certain embodiments, the present invention provides a system for ablation therapy, comprising a power distributor.

In certain embodiments, the present invention provides a system for ablation therapy, comprising a power distributor, a power splitter, and a device described herein (e.g., having a linear array of antenna components configured to emit energy from varied locations). In some embodiments, the power splitter is configured to provide the same power throughout the device. In some embodiments, the power splitter is configured to provide a different amount of power to different regions of the antenna, as so desired by the user or directed by a tuning element. In some embodiments, the system comprises more than one ablation device as described herein (e.g., having a linear array of antenna components configured to emit energy from varied locations) for purposes of, for example, phasing the energy delivery from the devices in a constructive or destructive manner. The devices of the present invention may be combined or utilized with any kind of additional ablation devices (see, e.g., U.S. Pat. Nos. 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/237,136, 11/236,985, 10/980,699, 10/961,994, 10/961,761, 10/834,802, 10/370,179, 09/847,181; U.S. Provisional Patent Nos. 60/785,690, 60/785,467, and 60/785,466; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties).

In certain embodiments, the present invention provides a method of treating a tissue region, comprising providing a tissue region and a device described herein (e.g., having a linear array of antenna components configured to emit energy from varied locations); positioning a portion of the device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the user is able to control the release of energy through different regions of the device and control the amount of energy delivered through each region of the device for purposes of precisely sculpting an ablation zone. In some embodiments, the tissue region is a tumor. In some embodiments, the tissue region comprises one or more of the heart, liver, genitalia, stomach, lung, skin, breast, large intestine, small intestine, brain, neck, bone, kidney, muscle, tendon, blood vessel, prostate, bladder, and spinal cord.

In some embodiments, energy is delivered to the tissue region in different intensities and from different locations within the device. For example, certain regions of the tissue region may be treated through one portion of the device, while other regions of the tissue may be treated through a different portion of the device. In addition, two or more regions of the device may simultaneously deliver energy to a particular tissue region so as to achieve constructive phase interference (e.g., wherein the emitted energy achieves a synergistic effect). In other embodiments, two or more regions of the device may deliver energy so as to achieve a destructive interference effect. In some embodiments, the method further provides additional devices for purposes of achieving constructive phase interference and/or destructive phase interference. In some embodiments, phase interference (e.g., constructive phase interference, destructive phase interference), between one or more devices, is controlled by a processor, a tuning element, a user, and/or a power splitter.

In some embodiments, the device is configured for percutaneous, intravascular, intracardiac, laparoscopic, endoscopic, or surgical delivery of energy. In some embodiments, the device is configured for delivery of energy to a target tissue or region. The present invention is not limited by the nature of the target tissue or region. The device may be rigid or flexible, and mounted on a number of different delivery tools including but not limited to: a percutaneous needle shaft, a laparoscope, an endoscope, intravascular catheters, etc.

The systems, devices, and methods of the present invention may be used in conjunction with other systems, device, and methods (see, e.g., U.S. Provisional Patent Nos. 60/785,466, 60/785,467, and 60/785,690, each of which is herein incorporated by reference in their entireties). For example, the systems, devices, and methods of the present invention may be used with other ablation devices, other medical devices, diagnostic methods and reagents, imaging methods and reagents, and therapeutic methods and agents. In some embodiments, the devices of the present invention may be mounted onto additional medical procedure devices. For example, the devices may be mounted onto endoscopes, intravascular catheters, or laproscopes. In some embodiments, the devices are mounted onto steerable catheters. Use may be concurrent or may occur before or after another intervention. The present invention contemplates the use systems, devices, and methods of the present invention in conjunction with any other medical interventions.

In some embodiments, the energy delivery systems of the present invention utilize coolant systems so as to reduce undesired heating within and along an energy delivery device (e.g., tissue ablation catheter). The systems of the present invention are not limited to a particular cooling system mechanism. In some embodiments, the systems are designed to circulate a coolant (e.g., air, liquid, etc.) throughout an energy delivery device such that the coaxial transmission line(s) and antenna(e) temperatures are reduced. In some embodiments, the systems utilize energy delivery devices having therein channels designed to accommodate coolant circulation. In some embodiments, the systems provide a coolant sheath wrapped around the antenna or portions of the antenna for purposes of cooling the antenna externally (see, e.g., U.S. patent application Ser. No.

11/053,987; herein incorporated by reference in its entirety). In some embodiments, the systems utilize energy delivery devices having a conductive covering around the antenna for purposes of limiting dissipation of heat onto surrounding tissue (see, e.g., U.S. Pat. No. 5,358,515; herein incorporated by reference in its entirety).

DETAILED DESCRIPTION

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy with a linear array of antenna components configured to emit energy from varied locations having optimized energy delivery characteristics. In certain embodiments, methods are provided for treating a tissue region (e.g., a tumor) through application of energy with the systems and devices of the present invention.

In preferred embodiments, the systems, devices, and methods of the present invention employ microwave energy. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction as it radiates through tissue, fluid/blood, as well as air. Therefore, microwave energy can be used in tissue, bone, lumens, lungs, and intravascularly.

The illustrated embodiments provided below describe the systems and devices of the present invention in terms of medical applications (e.g., ablation of tissue through delivery of microwave energy). However, it should be appreciated that the systems and devices of the present invention are not limited to medical applications. In addition, the illustrated embodiments describe the systems and devices of the present invention in terms of medical devices configured for tissue ablation. It should be appreciated that the systems and devices of the present invention are not limited to medical devices configured for tissue ablation. The illustrated embodiments describe the systems and devices of the present invention in terms of microwave energy. It should be appreciated that the systems and devices of the present invention are not limited to a particular type of energy (e.g., radiofrequency energy).

The systems and devices of the present invention provide numerous advantages over the currently available systems and devices. For example, a major drawback with currently available medical devices that utilize microwave energy is that the emitted energy is provided locally, thereby precluding delivery of energy over a deeper and denser scale. The devices of the present invention overcome this limitation by providing an applicator device having a linear array of antenna components configured to deliver energy (e.g., microwave energy) over a wider and deeper scale (e.g., as opposed to local delivery). Such a device is particularly useful in the tissue ablation of dense and/or thick tissue regions (e.g., tumors, organ lumens) and particularly deep tissue regions (e.g., large cardiac areas, brains, bones).

Certain preferred embodiments of the present invention are described below. The present invention is not limited to these embodiments.

Figure 1:
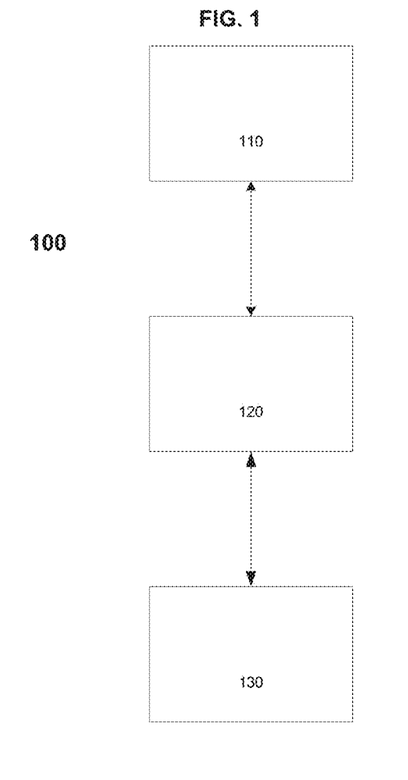
FIG. 1 shows a schematic view of a system for microwave therapy.

FIG. 1 shows a schematic view of a system for microwave therapy 100 configured for medical procedures (e.g., tissue ablation). In some embodiments, the system for microwave therapy 100 is configured to simultaneously deliver microwave energy from numerous vantage points (e.g., through a linear array of antenna components) thereby allowing the treatment (e.g., ablation) of dense and/or thick tissue regions (e.g., tumors, organ lumens) and particularly deep tissue regions (e.g., large cardiac areas, brains, bones). The system for microwave therapy 100 is not limited to a particular type of microwave therapy. Indeed, the system for microwave therapy 100 encompasses any type of microwave therapy (e.g., exposure of a tissue (e.g., cancer cells) to high temperatures so as to kill the tissue or to make the tissue more sensitive to alternative treatment forms (e.g., to render tissue more sensitive to the effects of radiation; to render tissue more sensitive to anticancer drugs)). In some embodiments, the system for microwave therapy 100 generally comprises a generator 110, a power distribution system 120, and an applicator device 130.

Still referring to FIG. 1, in some embodiments, the generator 110 serves as an energy source to the system for microwave therapy 100. In some embodiments, the generator 110 is configured to provide as much as 100 watts of microwave power of a frequency of 2.45 GHz, although the present invention is not so limited. The system for microwave therapy 100 is not limited to a particular type of generator 110. Exemplary generators that find use with the present invention include, but are not limited to, those available from Cober-Muegge, LLC, Norwalk, Connecticut, USA.

Still referring to FIG. 1, in some embodiments, the power distribution system 120 distributes energy from the generator 110 to the applicator device 130. The power distribution system 120 is not limited to a particular manner of collecting energy from the generator 110. The power distribution system 120 is not limited to a particular manner of providing energy to the applicator device 130. In some embodiments, the power distribution system 120 is configured to transform the characteristic impedance of the generator 110 such that it matches the characteristic impedance of the applicator device 130. In some embodiments, an impedance tuning component (not shown) is provided to permit continuous and variable impedance matching, as desired.

In some embodiments, the power distribution system 120 is configured with a variable power splitter so as to provide varying energy levels to different regions of a device (e.g., a linear array of antenna components configured to emit energy from varied locations). In some embodiments, the power splitter is used to feed multiple energy delivery devices with separate energy signals. In some embodiments, the power splitter electrically isolates the energy delivered to each energy delivery device so that, for example, if one of the devices experiences an increased load as a result of increased temperature deflection, the energy delivered to that unit is altered (e.g., reduced, stopped) while the energy delivered to alternate devices is unchanged. The present invention is not limited to a particular type of power splitter. In some embodiments, the power splitter is configured to receive energy from a power generator and provide energy to additional system components (e.g., energy delivery devices). In some embodiments the power splitter is able to connect with one or more additional system components (e.g., 1, 2, 3, 4, 5, 7, 10, 15, 20, 25, 50, 100, 500 . . . ). In some embodiments, the power splitter is configured to deliver variable amounts of energy to different regions within an energy delivery device for purposes of delivering variable amounts of energy from different regions of the device. In some embodiments, the power splitter is used to provide variable amounts of energy to multiple energy delivery devices for purposes of treating a tissue region. In preferred embodiments, the power splitter is configured to operate within a system comprising a processor, an energy delivery device, a temperature adjustment system, a power splitter, a tuning system, and/or an imaging system.

In some embodiments, where multiple antennas are employed, the system of the present invention may be configured to run them simultaneously or sequentially (e.g., with switching). In some embodiments, the system is configured to phase the fields for constructive or destructive interference. Phasing may also be applied to different elements within a single antenna.

Still referring to FIG. 1, in some embodiments, the applicator device 130 is configured to receive energy (e.g., microwave energy) from the power distribution system 120 and deliver the energy to a load (e.g., tissue region). In some embodiments, the applicator device 130 is configured to transform the characteristic impedance of the power distribution system 120 such that it matches the characteristic impedance level of the applicator device 130. In preferred embodiments, the applicator device 130 is configured to deliver microwave energy from a plurality of vantage points through a linear array of antenna components (described in more detail below). One skilled in the art will appreciate any number of alternative configurations that accomplish the physical and/or functional aspects of the present invention. The applicator device 130 is configured to deliver energy (e.g., microwave energy) to deep portions of a tissue from a plurality of vantage points (e.g., linear array of antenna components). The applicator device 130 is not limited to particular size dimensions. In some embodiments, the size of the applicator device 130 is designed for passage through a medical catheter and into a subject's internal body cavities (e.g., heart, brain, stomach, bone). In some embodiments, the applicator device 130 is designed for percutaneous insertion into a subject's body. The applicator device 130 is not limited to a particular length. In some embodiments, the length of the applicator device 130 is designed so as to maximize or minimize the emission of energy depending on a user's intention.

Figure 2:
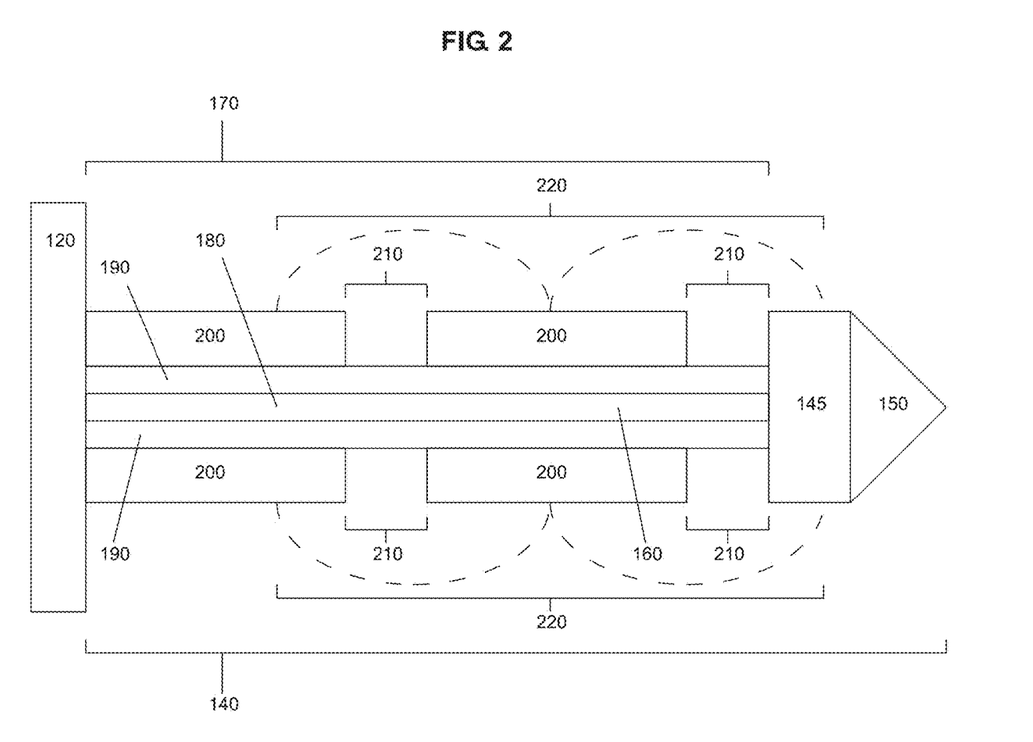
FIG. 2 shows a cross-section view of a device of the present invention.

FIG. 2 shows a schematic cross-section perspective of an applicator device 130 connected to a power distribution system 120. The applicator device 130 is not limited to particular configurations. In some embodiments, the applicator device 130 is shaped in a tubular configuration. The applicator device 130 is not limited to a particular length or width. In preferred embodiments, the configuration of the applicator device 130 is such that it is capable of delivering microwave energy to a load (e.g., a tissue region) from a plurality of vantage points. In some embodiments, the applicator device 130 comprises an antenna 140, a conductive terminal end 145, and, in some embodiments, a stylet 150.

Still referring to FIG. 2, the antenna 140 is configured to receive, transfer and emit microwave energy. The antenna 140 is not limited to particular size dimensions. The antenna 140 is not limited to receiving, transferring, or emitting a particular amount of microwave energy. The antenna 140 is not limited to receiving, transferring, or emitting microwave energy at a particular rate. In preferred embodiments, the antenna 140 is designed to simultaneously emit microwave energy from a plurality of vantage points thereby permitting the treatment (e.g., ablation treatment) of dense and/or thick tissue regions (e.g., tumors, organ lumens) and particularly deep tissue regions (e.g., large cardiac areas, brains, bones). In some embodiments, the antenna 140 comprises an inner conductor 160 and an outer conductor 170.

Still referring to FIG. 2, the inner conductor 160 is designed to receive, transfer and emit microwave energy. The inner conductor 160 is not limited to receiving, transferring, or emitting a particular amount of microwave energy. The inner conductor 160 is not limited to receiving, transferring, or emitting microwave energy at a particular rate. The inner conductor 160 is designed to receive and transfer microwave energy such that the transmission follows a wavelength pattern. The inner conductor 160 is not limited to particular size dimensions. In some embodiments, the length of the inner conductor 160 is consistent with the length of the antenna 140. The inner conductor 160 generally comprises a central transmission line 180 and a dielectric layer 190.

Still referring to FIG. 2, the central transmission line 180 is configured to receive, transfer and emit any amount of microwave energy, at any rate. The central transmission line 180 is not limited to particular size dimensions. In preferred embodiments, the length of the central transmission line 180 is consistent with the length of the antenna 140. In some embodiments, the antenna is configured to conduct cooling fluid along its length via any mechanism, including, but not limited to, flowing coolant through chambers or channels (e.g., in the dielectric material 190) or around the outer surface of the antenna. In some embodiments, the central transmission line 180 is hollow. In some embodiments, the central transmission line 180 has a diameter of, for example, 0.012 inches.

Still referring to FIG. 2, a dielectric layer 190 is provided. The dielectric layer 190 is not limited to particular size dimensions. In some embodiments, the material of the dielectric layer 190 has near-zero conductivity (e.g., air, gas, fluid). In some embodiments, the material of the dielectric layer 190 is rigid (e.g., ceramic, fiberglass, etc.) while maintaining near-zero conductivity. In some embodiments, the dielectric layer 190 is coated with a heat-resistant coating (e.g., Teflon).

Still referring to FIG. 2, an outer conductor 170 is provided. The outer conductor 170 is not limited to particular size dimensions. The outer conductor 170 is not limited to a particular type of material (e.g., metal, plastic, ceramic, etc.). In some embodiments, the outer conductor 170 is coated with a heat-resistant coating (e.g., Teflon). In preferred embodiments, the outer conductor 170 is provided in two or more outer conductor segments 200 separated by gaps 210.

Still referring to FIG. 2, the outer conductor segments 200 are not limited to a particular length. The outer conductor 170 is not limited to a particular number of outer conductor segments 200 (e.g., 2, 3, 4, 5, 10, etc.). In some embodiments, the outer conductor 170 has therein two outer conductor segments 200. In some embodiments, the length of the outer conductor segments 200 corresponds to the distance of a half—wavelength (λ/2) of microwave energy transmitting through the inner conductor 160. In some embodiments, the length of the outer conductor segments 200 are varied.

Still referring to FIG. 2, the outer conductor segment gaps 210 are designed to permit emission of microwave energy transmitting through the antenna in desired locations. The outer conductor 170 is not limited to a particular number of outer conductor segment gaps 210 (e.g., 2, 3, 4, 5, 10, etc.). The outer conductor segment gaps 210 are not limited to particular size dimensions. In some embodiments, the gaps entirely circumscribe the outer conductor, while in other embodiments, the gaps only partially circumscribe the outer conductor (e.g., 180 degrees, 270 degrees, 90 degrees, etc.). In the latter case, such embodiments find use for unidirectional operation (e.g., for cardiac ablation). In some embodiments, the partially circumscribing gaps are alternated (e.g., one gap on one side of the circumferences, the next gap on the other side). In some embodiments, the spacing and width of the gaps are varied so as to ensure even heating along the antenna. In some embodiments, the size of the gaps is varied so as to alter the homogeneity of the energy distribution. For example, in some embodiments, smaller gaps at the proximal end of the device are provided to allow energy to be delivered to larger gaps at the distal end. In some embodiments, several small gaps are used with different element lengths between them, typically each being less than one wavelength, to alter the homogeneity of the field intensity pattern. Thus, configuration may be optimized for deep field penetration, for shallow heating, etc. In preferred embodiments, the size of the outer conductor segment gaps 210 is such that microwave energy transmitting by the antenna is permitted to peak in desired locations defined by the location of the segments 200 and gaps 210 (e.g., for purposes of tissue ablation). The outer conductor segment gaps 210 are not limited to a particular position along the outer conductor 170. In some embodiments, the outer conductor segment gaps 210 are positioned along the outer conductor 170 so as to coincide with the wavelength peaks of the microwave energy transmitting along the antenna (e.g., for purposes of maximum microwave energy emission). In some embodiments, the outer conductor segment gaps 210 are filled with a material to prevent accumulation of tissue or fluid within the gap. In preferred embodiments, the outer conductor segment gaps 210 are filled with a material to prevent accumulation of tissue or fluid within the gap, while not precluding emission of the microwave energy transmitting along the inner conductor 160. Dielectric material may be used to fill the gaps to provide a uniform, smooth outer surface.

As demonstrated in FIG. 2, the outer conductor 170 has therein two outer conductor segments 200 and two outer conductor segment gaps 210. FIG. 2 shows an exemplary energy emission pattern 220. As shown, the energy emission pattern 220 reaches a peak of intensity near the center of each conductor segment gap 210, and diminishes in intensity near the edges of each conductor segment gap 210. In some embodiments, two or more outer segment gaps are positioned in close proximity so as to achieve a combined energy emission (e.g., a cumulative effect, constructive phase interference, destructive phase interference) over a contiguous or nearly contiguous length of the antenna (described in more detail below).

Still referring to FIG. 2, the distal end of the inner conductor 160 engages a conductive terminal end 145. The conductive terminal end 145 is not limited to particular size dimensions. In some embodiments, the diameter of the conductive terminal end 145 is consistent with outer diameter of the outer conductor 170. The conductive terminal end 145 is not limited to a particular shape. In some embodiments, the conductive terminal end 145 has a disc shape.

Still referring to FIG. 2, the conductive terminal end 145 engages a stylet 150. The applicator 130 is not limited to a particular stylet 150. In some embodiments, the stylet 150 is designed to facilitate percutaneous insertion of the applicator 130.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249; each herein incorporated by reference in their entireties.

In some embodiments, the device is configured to attach with a detachable handle. The present invention is not limited to a particular type of detachable handle. In preferred embodiments, the detachable handle is configured to connect with multiple devices (e.g., 1, 2, 3, 4, 5, 10, 20, 50 . . . ) for purposes of controlling the energy delivery through such devices.

In some embodiments, the device is designed to physically surround a particular tissue region for purposes of energy delivery (e.g., the device may be flexibly shaped around a particular tissue region). For example, in some embodiments, the device may be flexibly shaped around a blood vessel (e.g., pulmonary vein) for purposes of delivering energy to a precise region within the tissue.

In use, the applicator device is particularly useful for tissue ablation of dense and/or thick tissue regions (e.g., tumors, organ lumens) and particularly deep tissue regions (e.g., large cardiac areas, brains, bones). Indeed, the applicator device may be positioned inside or in the vicinity of a tissue requiring a tissue ablation (e.g., a tumor). Whereas standard ablation instruments only permit localized delivery of microwave energy to a tissue to be treated, the devices of the present invention can simultaneously deliver energy to a plurality of locations or a broader area within the tissue. In some embodiments, the devices of the present invention are used in the ablation of a tissue region having high amounts of air and/or blood flow (e.g., lung tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

In addition, the devices of the present invention are configured to deliver energy from different regions of the device (e.g., outer conductor segment gaps) at different times (e.g., controlled by a user) and at different energy intensities (e.g., controlled by a user). Such control over the device permits the phasing of energy delivery fields for purposes of achieving constructive phase interference at a particular tissue region or destructive phase interference at a particular tissue region. For example, a user may employ energy delivery through two (or more) closely positioned outer conductor segments so as to achieve a combined energy intensity (e.g., constructive phase interference). Such a combined energy intensity may be useful in particularly deep or dense tissue regions. In addition, such a combined energy intensity may be achieved through utilization of two (or more) devices. In some embodiments, phase interference (e.g., constructive phase interference, destructive phase interference), between one or more devices, is controlled by a processor, a tuning element, a user, and/or a power splitter.

The systems and devices of the present invention may be combined within various system/kit embodiments. For example, the present invention provides kits comprising one or more of a generator, a power distribution system, an applicator, along with any one or more accessory agents (e.g., surgical instruments, software for assisting in procedure, processors, temperature monitoring devices, etc.). The present invention is not limited to any particular accessory agent. Additionally, the present invention contemplates kits comprising instructions (e.g., ablation instructions, pharmaceutical instructions) along with the systems and devices of the present invention and/or a pharmaceutical agent (e.g., a sedating medication, a topical antiseptic, a topical anesthesia).

The devices of the present invention may be used in any medical procedure (e.g., percutaneous or surgical) involving delivery of energy (e.g., microwave energy) to a tissue region. The present invention is not limited to a particular type or kind of tissue region (e.g., brain, liver, heart, breast, skin, blood vessels, foot, lung, bone, etc.). For example, the systems of the present invention find use in ablating tumor regions. In such uses, the applicator device is inserted into, for example, a subject such that the linear array of antenna components are positioned in the vicinity of and/or within a desired tissue region (e.g., a dense tumor). Next, the generator is used to provide a desired amount of microwave energy to the power distribution system at a characteristic impedance level, which in turn provides the energy at a characteristic impedance level to the applicator. Next, a desired amount of microwave energy is delivered to the desired tissue region (e.g., tumor) through the outer conductor segment gaps within the outer conductor (see, e.g., FIG. 2), thereby generating a plurality of electric fields of sufficient strength to ablate the desired tissue region. In some embodiments, all of the outer conductor segment gaps are utilized to deliver energy, while in other embodiments, only a limited number (e.g., at least one) of the outer conductor segment gaps are utilized to deliver energy. In some embodiments, maximum energy is delivered through the outer conductor segment gaps, while in other embodiments, the intensity of energy delivered through the outer conductor segment gaps is varied depending on the tissue region being treated and the user's (e.g., physician's) discretion. Due to multiple energy emissions permitted with the devices of the present invention, the devices of the present invention permit treatment (e.g., ablation treatment) of dense, long, and/or thick tissue regions (e.g., tumors, organ lumens) and particularly deep tissue regions (e.g., large cardiac areas, brains, bones) in a manner superior to standard ablation devices (e.g., through constructive phase interference and/or destructive phase interference). In addition, the devices of the present invention may be combined with additional ablation devices or features of other ablation devices (see, e.g., U.S. Provisional Patent Nos. 60/785,466, 60/785,467, and 60/785,690, each of which is herein incorporated by reference in their entireties). In some embodiments, the present invention further provides software for regulating the amount of microwave energy provided to a tissue region through monitoring of the temperature of the tissue region (e.g., through a feedback system). In such embodiments, the software is configured to interact with the systems for microwave therapy of the present invention such that it is able to raise or lower (e.g., tune) the amount of energy delivered to a tissue region. In some embodiments, the type of tissue being treated (e.g., liver) is inputted into the software for purposes of allowing the software to regulate (e.g., tune) the delivery of microwave energy to the tissue region based upon pre-calibrated methods for that particular type of tissue region. In other embodiments, the software provides a chart or diagram based upon a particular type of tissue region displaying characteristics useful to a user of the system. In some embodiments, the software provides energy delivering algorithms for purposes of, for example, slowly ramping power to avoid tissue cracking due to rapid outgassing created by high temperatures. In some embodiments, the software allows a user to choose power, duration of treatment, different treatment algorithms for different tissue types, simultaneous application of power to the antennas in multiple antenna mode, switched power delivery between antennas, coherent and incoherent phasing, etc.

In some embodiments, the software is configured for imaging equipment (e.g., CT, MM, ultrasound). In some embodiments, the imaging equipment software allows a user to make predictions based upon known thermodynamic and electrical properties of tissue and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the devices of the present invention may be mounted onto additional medical procedure devices. For example, the devices may be mounted onto endoscopes, intravascular catheters, or laproscopes. In some embodiments, the devices are mounted onto steerable catheters. Any desirable configuration may be used. In some embodiments, a flexible catheter is mounted on an endoscope, intravascular catheter or laparoscope. For example, the flexible catheter, in some embodiments, has multiple joints (e.g., like a centipede) that permits bending and steering as desired to navigate to the desired location for treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A device consisting of an antenna, a stylet, and a conductive terminal end having a conductive terminal end proximal end and a conductive terminal end distal end, wherein said antenna comprises an outer conductor enveloped around an inner conductor, wherein said inner conductor is designed to receive and transmit microwave or radiofrequency energy, wherein the inner conductor is hollow, wherein said outer conductor has therein a plurality of gaps positioned circumferentially along said outer conductor, wherein multiple energy peaks are configured to be generated along a length of said antenna, wherein positions of said multiple energy peaks are controlled by a location of said plurality of gaps, wherein a distal end of the inner conductor is closed, wherein the stylet engages the conductive terminal end distal end, wherein one of the plurality of gaps is positioned circumferentially along said outer conductor between a distal end of the outer conductor and the conductive terminal end proximal end, wherein the conductive terminal end comprises a disc having a diameter substantially identical to a diameter of the outer conductor.

2. The device of claim 1, wherein the antenna is flexible.

3. The device of claim 1, wherein the material of the outer conductor from a proximal end of the outer conductor to the distal end of the outer conductor distal end is the same.

4. The device of claim 1, wherein each of the plurality of gaps has a proximal end and a distal end, wherein one of the plurality of gaps is positioned most distally along the length of the antenna.

5. The device of claim 1, wherein said antenna comprises a dielectric layer disposed between said inner conductor and said outer conductor, wherein the dielectric layer has a proximal end and a distal end.

6. The device of claim 5, wherein the antenna is configured to conduct cooling fluid along its length through one or more channels, wherein the one or more channels have a proximal end and a distal end, wherein the distal end of the one or more channels engages the conductive terminal end proximal end, wherein the distal end of the one more channels is closed.

7. The device of claim 5, wherein the dielectric layer distal end and the inner conductor distal end each engage but do not extend into the conductive terminal end proximal end.

8. The device of claim 1, wherein said plurality of gaps is at least two gaps.

9. The device of claim 1, wherein said inner conductor has a diameter of approximately 0.013 inches or less.

10. The device of claim 1, further comprising a tuning element for adjusting an amount of the microwave or radiofrequency energy delivered.

11. A system for ablation therapy, consisting of a power distributor and the device of claim 1.

12. A method of treating a tissue region, comprising:
a) providing the device of claim 1;
b) positioning said device in a vicinity of a tissue region,
c) delivering an amount of the microwave or radiofrequency energy with said device to said tissue region.

* * * * *